(12) United States Patent
Steer

(10) Patent No.: US 6,241,712 B1
(45) Date of Patent: Jun. 5, 2001

(54) OSTOMY APPLIANCES

(75) Inventor: Graham E. Steer, London (GB)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/151,424

(22) Filed: Sep. 11, 1998

(30) Foreign Application Priority Data

Sep. 18, 1997 (GB) .................................................. 9719923
Sep. 18, 1997 (GB) .................................................. 9719925

(51) Int. Cl.[7] ...................................................... A61F 5/44
(52) U.S. Cl. ............................................................ 604/333
(58) Field of Search ...................................... 604/332–345

(56) References Cited

U.S. PATENT DOCUMENTS

| | | | |
|---|---|---|---|
| 4,211,224 | * 7/1980 | Kubach et al. | 604/333 |
| 4,232,672 | * 11/1980 | Steer et al. | 604/333 |
| 5,643,234 | * 7/1997 | Lesko | 604/333 |
| 5,672,163 | * 9/1997 | Ferreira et al. | 604/333 |
| 5,733,271 | * 3/1998 | Bjorn | 604/333 |
| 5,840,073 | * 11/1998 | Olsen | 604/333 |

* cited by examiner

Primary Examiner—Dennis Ruhl
Assistant Examiner—Carie Mager
(74) Attorney, Agent, or Firm—Stuart E. Krieger

(57) ABSTRACT

An ostomy pouch coupling member includes a filter assembly having a filter housing with a bore. A filter element is insertable into the bore, and is ejectable from the bore into the ostomy pouch by pushing the filter element. The filter element may be made of superabsorbent material.

4 Claims, 6 Drawing Sheets

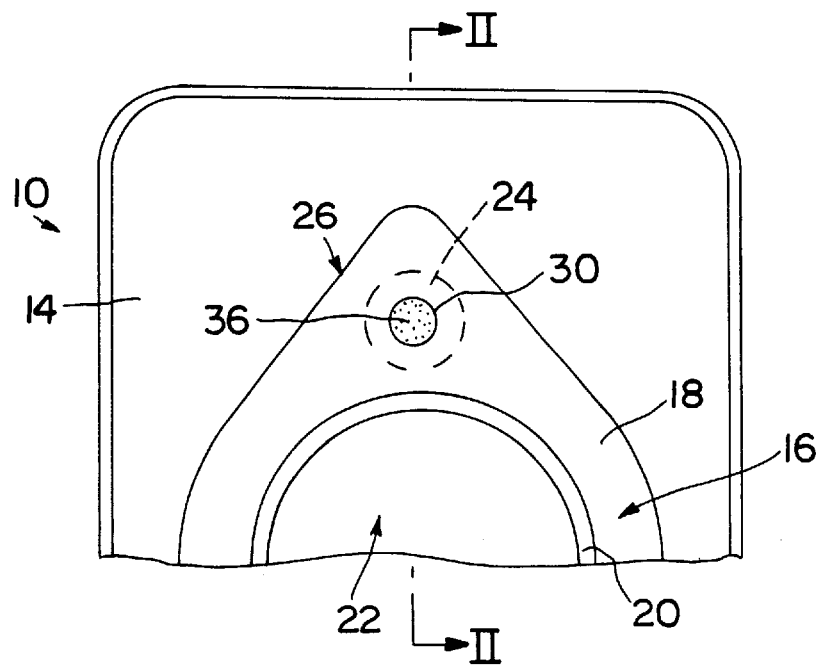
FIG. 1
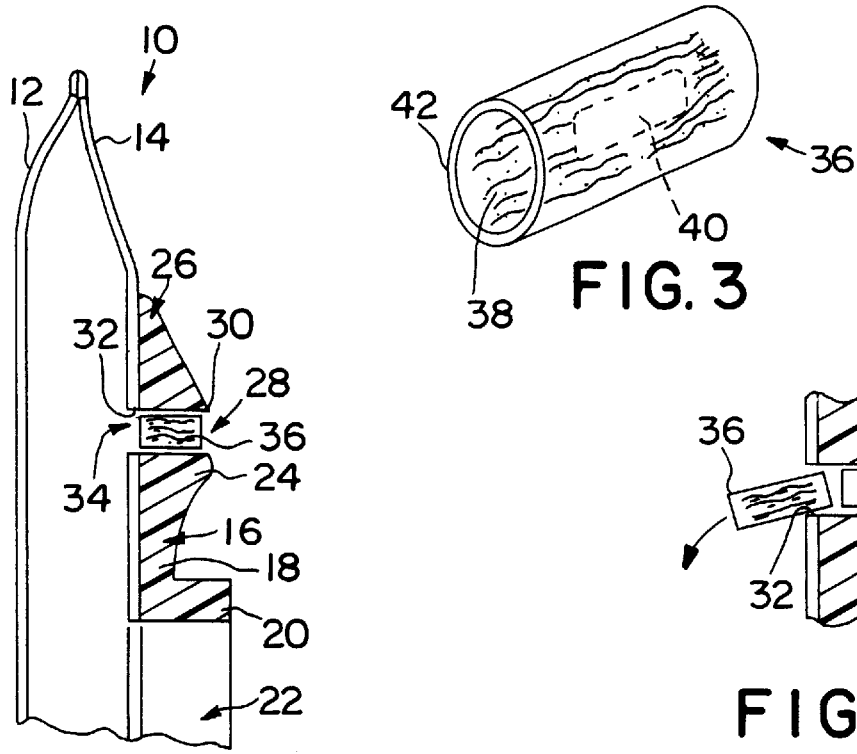
FIG. 2
FIG. 3
FIG. 4

OSTOMY APPLIANCES

BACKGROUND OF THE INVENTION

This invention relates generally to ostomy appliances. In on aspect, the invention relates to a deodorising filter arrangement for an ostomy pouch. In another aspect, the invention relates to a superabsorbent member suitable for use in an ostomy pouch, and also to a method of introducing the superabsorbent member into a pouch. This aspect of the invention is particularly suitable for use with ileostomy pouches or urostomy pouches, but it is not limited only to such applications.

DESCRIPTION OF THE PRIOR ART

The prior art is replete with suggestions intended to permit flatus gasses to be vented from an ostomy pouch. Many such arrangements include means for deodorising these gases by the use of filters of various kinds.

For example, reference is made to the arrangements proposed in GB-A-2,225,952 and U.S. Pat. No. 4,451,258 (both E. R. Squibb and Sons, Inc.) and GB-A-2,177,926 (Craig Medical Products Limited). Further reference is made to WO-A-96/10378, EP-A-0709076, and U.S. Pat. No. 4,211,224.

SUMMARY OF THE INVENTION

Such designs can provide advantages to the ostomate, for example, in terms of flow rate adjustability and filter replacement. Nevertheless, there remains a need for further compact, simple and effective filter arrangements which can be manufactured economically.

In contrast to many conventional filter elements in which a flat filter is received within a flat filter housing, one aspect of the present invention is to employ a filter housing having a bore therein, and an elongate deodorising filter element received or receivable longitudinally within the bore. The bore preferably has a longitudinal dimension greater than its, or a, lateral dimension. Preferably, in use, the gas flow through the deodorising filter element is generally in an axial direction.

For the avoidance of doubt, the term elongate is used herein broadly to mean that the length is greater than the, or a, lateral dimension.

During the development work leading to this aspect of the invention, it was appreciated that compact filters are already mass produced in the cigarette filter industry. Although conventional cigarette filters themselves might not be fully effective in deodorising the unpleasant odours of flatus gasses, for example, sulphur dioxide to which the human nose is extremely sensitive, the production facilities may nevertheless be suitable for the production of ostomy deodorising filters. In contrast to the prior art, the invention enables advantage to be taken for the first time of the existing production facilities used in the cigarette filter industry to mass produce elongate, compact ostomy filters very economically. To the best of the inventor's knowledge and belief, such a filter type or construction has not been contemplated for ostomy use hitherto.

Preferably, the bore and the filter element are generally cylindrical, although this is not essential in all embodiments.

Preferably, the bore is generally straight. The ends of the bore may be generally transverse to the axis of the bore, or one or both ends may be inclined relative to the axis. In the former case, the bore is preferably of about the same length as the filter element, whereas in the latter case, the bore is preferably longer than the filter element (to ensure that the filter element is contained within the bore along its entire length.

Preferably, the filter element is a snug fit within the bore, and is retained in position by frictional engagement between the filter and the inner surface of the bore. One or more projections may be provided on the inner surface of the bore to grip the filter element. Alternatively, or additionally, one or more end members, for example, end covers, may be employed to contain the filter within the bore.

In one preferred form, the filter element can be positioned within the bore manually by being slid into the bore through one end. Preferably, this can be performed by the ostomate while wearing the pouch, or prior to wearing the pouch.

In a particularly preferred form, an existing filter element positioned within the bore is displaceable, or ejectable, through one end of the bore by insertion of a new filter element through the opposite end. This can allow simple filter replacement without a person having to open, and then re-secure, the filter housing to access the filter element as in many prior art designs (which in some cases may require considerable dexterity).

More preferably, the bore is arranged with one end opening into the pouch, so that the ejected filter element can drop into the pouch. This is particularly advantageous, because it can enable filter replacement without the ostomate having to handle and dispose of the old filter. It will be appreciated that after some time in use, a filter may normally accumulate faecal matter, or slurry, on its surface, particularly if the pouch is almost full, or if the faecal matter has leaked into the filter compartment for other reasons. Handling such contaminated filters presents a hygiene risk. Moreover, it may not always be convenient to dispose of the old filter.

Another preferred feature is that a range of different filter elements be provided to enable an ostomate to select a filter with an optimum flow rate characteristic. The flow rate characteristic may be controlled by varying, for example, the filter density, pore density, or the tortuosity through the filter. The pouch may be supplied with a packet of such different filter elements, or the ostomate may be able to purchase a packet of different, or the same, filter elements separately. The ostomate can then insert the desired filter element into the housing prior to wearing the pouch. The filter elements may, for example, be coloured differently to indicate different flow rates.

In one preferred form, the filter housing is incorporated within a coupling member of an ostomy coupling. The filter is preferably incorporated in the bag-side coupling member, but could also be incorporated within the bodyside coupling member if desired.

In a further aspect, the invention provides a deodorising ostomy filter, comprising:

a filter housing having a bore therein, the bore having a longitudinal dimension greater than a lateral dimension; and an elongate filter element received or receivable longitudinally within the bore.

Preferably, the gas flow path within the bore is in one or more generally axial directions.

Preferably, the bore and the filter element are generally cylindrical.

Preferably, the filter element is insertable into one end of the bore. More preferably, the filter element is ejectable through one end of the bore by insertion of a replacement filter element through the opposite end.

In a further closely related aspect, the invention provides an ostomy pouch including a deodorising filter, the deodorising filter comprising:

a filter housing having a bore therethrough, the bore including an inner end communicating with an interior space of the pouch, and an opposite outer end;

an elongate filter element receivable longitudinally within the bore to deodorise gas escaping through the bore, the filter element being ejectable through the inner end of the bore into the pouch by insertion of a displacing object through the outer end of the bore.

Preferably, the object is a replacement filter element.

In a yet further related aspect, the invention provides an ostomy deodorising filter element, the element being generally cylindrical and having an axial length greater than its radial dimension, and preferably greater than is diameter. Preferably, the filter element is relatively rigid. The filter element may be encased in a sleeve to assist retention of the element's shape. The sleeve may be rigid or semi-rigid. The sleeve may be of a water-soluble material, for example, polyvinyl alcohol.

Preferably, the filter element contains superabsorbent material for absorbing any liquid which leaks or soaks into the filter element. This is particularly advantageous for filter or pouch configurations in which no protective barrier is provided to obstruct the passage of liquid into the filter.

In a yet further closely related aspect, the invention provides a method of replacing a filter element in a pouch having a filter housing in a bore of which is received an elongate filter element, the method comprising:

ejecting the existing filter through an inner end of the bore by insertion of an object through an opposite outer end of the bore to push the existing filter through the inner end and into the pouch; and inserting a replacement filter into the bore through the outer end.

The above method steps may be performed separately, but preferably are carried out simultaneously as a single method step of inserting a new filter element into the bore, which acts as an object to push the existing filter from the bore and into the pouch.

In a yet further related aspect, the invention provides a method of replacing a filter element in a pouch having a filter housing in a bore of which is received an elongate filter element, the method comprising:

inserting longitudinally into a first end of the bore a replacement filter element; and advancing the replacement filter element into the bore to displace the existing filter element and eject it through an opposite second end of the bore.

In a yet further aspect, the invention provides a method of forming deodorising filter elements for ostomy pouches, the method comprising forming an elongate rod of filter material, and cutting or slicing the rod into discrete elements.

The elements may have a transverse dimension which is less than the, or a longitudinal dimension, as described above. Alternatively, the elements may be in the form of slices having a transverse dimension greater than their axial thickness. Such elements could then be used a filter "discs" or layers in a conventional filter envelope of an ostomy pouch.

Preferably, the filter elements are generally cylindrical.

In a yet further aspect, the invention provides an ostomy pouch comprising a filter as aforesaid in any preceding aspect. The filter may either be received within a plastics housing, or it may received within an envelope or compartment formed by one or more sheets of plastics film, or it may be attached directly to a wall of the pouch.

In a yet further aspect relating to superabsorbent members, there have been a number of proposals to use superabsorbent material to gel the liquid contents of a pouch, for example, either a urostomy pouch or an ileostomy pouch. For example, reference is made to GB-A-2 268 882 (E.R. Squibb & Sons Inc.) in which a urostomy pouch is disclosed into which can be inserted a superabsorbent sheet to gel the urine in the pouch. Such an effect can increase customer acceptance and confidence in the pouch, because the gelled urine will not tend to slosh about in the pouch in the same way as liquid urine. Such sloshing is noisy and embarrassing for the wearer, and can raise doubts in the wearer's mind as to whether the pouch is attached securely.

However, urostomy pouches normally employ a non-return valve in their uppermost region, through which the superabsorbent material has to be inserted. The valve is commonly formed by welds which hold the pouch walls together. The effect is to allow liquid entering the pouch to dribble through the valve under gravity, but substantially avoid any liquid in the pouch from splashing back through the valve as the wearer moves about. The above mentioned GB-A-2 268 882 describes a tubular applicator with which the superabsorbent sheet can be inserted through the non-return valve in rolled-up form. Although such a technique can solve many of the problems in the art, it would be desirable to facilitate introduction of a superabsorbent material without the need, and expense, of a separate applicator.

Generally, ileostomy pouches do not employ a non-return valve, but it can nevertheless be quite difficult for a user to insert a superabsorbent sheet into the pouch, particularly for small diameter aperture pouches. Moreover, such pouches are often emptyable, and will require a new superabsorbent sheet to be inserted for each new use. It can be difficult for a user to insert the sheet without his or her hands contacting the inner surface of the pouch which may be fouled with ileostomy slurry. Such contact is unhygenic, unpleasant and embarrassing for the wearer.

The present invention has been devised bearing the above problems in mind.

In contrast to the prior art, one aspect of the invention is to provide a superabsorbent member (i.e. a member comprising or containing superabsorbent material) in a rigid or semi-rigid, elongate, stick or rod form.

Such a stick or rod can simply be inserted by hand endwise through the aperture and non-return valve of a urostomy pouch, without becoming fouled by the valve, and without the need for an applicator. When used for such an application, the member is preferably at least sufficiently rigid that it can be forced through the non-return valve.

The stick or rod can also be inserted easily into an ileostomy pouch, and manoeuvred and manipulated more easily into position, without the user having to touch the inner surface of the pouch.

Preferably, the superabsorbent member is made substantially entirely of one or more water gellable materials and/or of one or more water soluble materials. When the member comes into contact with liquid (e.g. urine in the pouch), the member can disintegrate without leaving any solid parts behind. This can avoid any solid parts in the pouch contents when the pouch is, for example, emptied into a toilet in a conventional manner.

In one form, the superabsorbent member is formed in a similar manner to a conventional cigarette filter. Granules, or powder-like micro-granules, of superabsorbent material can be packed into, or distributed in or on a wad of material to form, an elongate stick or rod using processing similar to that used conventionally in the cigarette filter production industry.

A particular advantage is that such members may be produced using the existing, proven production facilities already used in the cigarette filter industry, with little, if any, modifications being required to produce a batch of superabsorbent containing members.

The superabsorbent may be carried on material which is itself water soluble. For example, a suitable material may be polyvinyl alcohol PVOH (either in film, fibre or filament form).

The member may comprise an outer sleeve or case to protect and maintain the shape of the stick or rod member. Preferably, the sleeve or case is of water soluble material, for example, polyvinyl alcohol.

The member may alternatively comprise a sleeve or case containing superabsorbent granules. The sleeve or case may be of a water soluble material, for example, polyvinyl alcohol.

Superabsorbent materials are known per se, and are available from a number of different manufacturers. An example is the material Salsorb CL10 produced by Allied Colloids.

It will also be appreciated that other "active" materials, such as odour counteractants, disinfectants, and preservatives, may be included in the member.

In another aspect, the invention provides a member as aforesaid, and an ostomy pouch having an opening (either a permanent opening, or a closable opening) through which the member can be introduced into the pouch. The opening may, for example, be the stoma aperture, or it may, for example, be a closable drain.

In another aspect, the invention provides a pouch (for example, a urostomy pouch) and a superabsorbent or superabsorbent-containing member, the urostomy pouch comprising an inlet aperture and a non-return (or anti-splash) valve adjacent to the aperture, and the member being provided in the form of a rigid or semi-rigid, elongate, stick or rod, the member being directly insertable through the aperture and the non-return valve into the liquid collecting chamber of the pouch.

Preferably, the length of the member is greater than the minimum distance between the aperture and the non-return valve.

In a yet further aspect, the invention provides a method comprising:

providing a urostomy pouch having an inlet aperture and a non-return valve adjacent to the aperture;

providing a superabsorbent or superabsorbent-containing member in the form of a rigid or semi-rigid, elongate, stick or rod; and inserting the member endwise through the aperture and through the non-return valve, into the liquid collecting region of the pouch.

In a yet further aspect, the invention provides a method comprising:

providing an ostomy pouch having a (permanent or closable) opening;

providing a superabsorbent or superabsorbent-containing member in the form of a rigid or semi-rigid, elongate, stick or rod; and inserting the member endwise through the opening and into the collecting region of the pouch.

Although the above aspects may be used independently, further developments can be obtained by using two or more of the above aspects in combination.

BRIEF DESCRIPTION OF THE DRAWINGS

Embodiments of the invention are now described by way of example only, with reference to accompanying drawings, in which:

FIG. 1 is a rear view of a first embodiment used on an ostomy pouch;

FIG. 2 is a schematic sectional view along the line II—II of FIG. 1;

FIG. 3 is a schematic perspective view of a filter element in isolation;

FIG. 4 is a schematic sectional view similar to FIG. 2, but showing filter replacement;

DETAILED DESCRIPTION OF THE DRAWINGS

Figure 5:
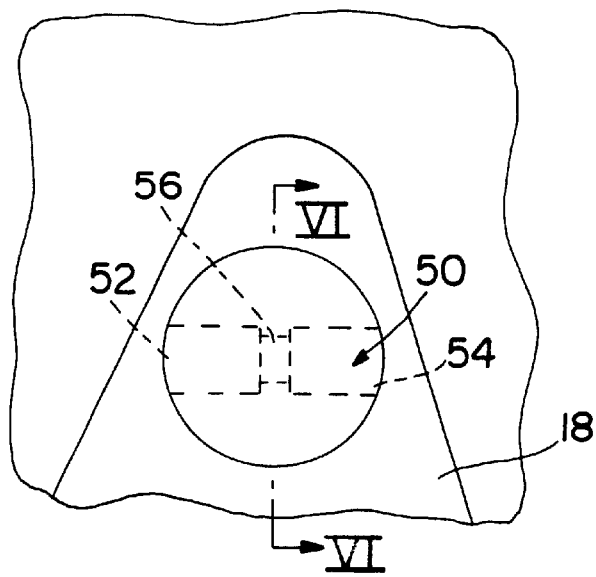
FIG. 5 is a rear partial view of a second embodiment.

Referring to FIGS. 1 and 2, an ostomy pouch 10 comprises a front wall 12 and a rear wall 14 of plastics film welded together around their periphery. A plastics bag-side coupling member 16 is welded to the rear wall 14 of the pouch as one half of a mechanical coupling for securing the pouch to a conventional body-side coupling member (not shown) attachable to the peristomal area of the ostomate by means of a conventional adhesive pad (not shown).

In the present embodiment, the bag-side coupling member 16 consists of a generally flat flange 18 from which projects a generally cylindrical wall 20 surrounding the stomal aperture 22 of the pouch 10. Although not illustrated in detail, the cylindrical wall 20 may be formed with, or support, a locking or latching element for engaging the body-side coupling member. Such elements are well known in the art, the reader being referred in particular to the snap-together coupling described in GB 1571657, and to the split-locking ring couplings described in EP 0737456 and EP 0737458.

The design of the pouch as thus far described is largely conventional to those skilled in the art.

A filter housing 24 is integrally moulded in an enlarged uppermost portion 26 of the flange 18 (i.e. uppermost when the pouch is viewed in its normal orientation). The filter housing 24 consists of a raised profile through which extends a generally cylindrical bore 28. The bore has an outer end, or mouth, 30 open to the external atmosphere, and an inner end 32 which is open to the interior of the pouch through a vent aperture 34 in the rear wall 14 of the pouch. The axial length of the bore is greater than the bore radius (and, in this embodiment, greater than the bore diameter).

An elongate, generally cylindrical filter element 36 is received longitudinally within the bore 28. The filter element 36 is dimensioned to be a fairly snug fit within the bore 28 and, in use, is held in position by friction. If desired, one or more projecting ribs (not shown) may be provided on the inside face of the bore 28 to increase the grip on the filter element 36.

Referring to FIG. 3, the filter element 36 consists of a cylindrical pack or wad 38 of suitable filter material such as activated carbon, or a material containing or carrying activated carbon. The wad may be at least slightly compressible to enable it to be received as a tight fit within the bore 28. In this embodiment, there is no gas-permeable, liquid-impermeable wall in the pouch to prevent liquid from coming into contact with the filter. Accordingly, it is preferred that that the filter contains superabsorbent (liquid swellable) material to absorb any liquid which leaks into the filter element 36. This can substantially prevent, or at least delay, the passage of liquid soaking through the filter material, and thereby increase the effective life of the filter.

A suitable superabsorbent material is a crosslinked hydrophilic polymer, for example, sodium polyacrylate. The superabsorbent may either be distributed throughout the filter material, or it may be a discrete mass (depicted in phantom by numeral 40) received, for example, within a recess or pocket of the wad 38. In this embodiment, the wad 38 is surrounded by a cylindrical sleeve 42, for example, of paper or plastics film (for example, water soluble plastics (PVOH), to contain and protect the wad, and to provide the element with a degree of rigidity. The sleeve 42 is preferably of a flexible material, rather than a rigid shell.

Depending on the amount, and the configuration, of the superabsorbent in the filter element 36, the swelling of the superabsorbent upon absorption of liquid could be used to block the filter once the superabsorbent has reached absorption saturation; the resulting ballooning of the pouch caused by trapped gas unable to vent through the filter, would then indicate to the ostomate that the filter needs replacing, as described further below.

The filter element 36 is typically between about 1 cm and about 3 cm in length, with a diameter of between about 0.5 cm and about 1 cm. The bore 28 has dimensions corresponding roughly to those of the filter, so that the raised portion of the housing does not need to project from the face of the pouch unnecessarily, and to provide the friction retention of the filter within the bore. Although not illustrated in the drawings, the flange 16 may have a rear projection which projects into the interior of the pouch. This would enable the "height" of the exterior projection to be reduced, and could also provide a separation function to prevent the walls of the pouch from sticking together.

It has been appreciated during the work leading to the present invention that such an elongate, cylindrical, activated-carbon-containing and/or superabsorbent-containing filter can be produced using the conventional production facilities in the cigarette industry. This can enable suitable compact filters to be mass produced very economically. Generally, the filters would be produced as a continuous, or elongate rod, which is then cut or sliced into discrete filter elements.

Typically, the filter wad would then comprise a plurality of fibres or filaments packed together closely, and aligned generally in the longitudinal direction. In one form, the wad and/or the sleeve include or define one or more recesses or chambers for receiving the deodorising material. In another form, the filaments could comprise, or carry, the deodorising material.

Referring to FIG. 4, when it is desired to replace the filter element 36, a fresh filter element 44 is simply inserted through the mouth 30 of the bore 28. As the new filter element 44 is advanced into the bore 28, it contacts the existing filter element 26 and pushes it rearwards to be discharged or ejected through the inner end 32 of the bore. The discharged filter element 36 falls into the pouch, leaving the fresh filter element 44 in place in the bore 28. It will be appreciated that such filter replacement is extremely simple, and there is no need to dispose separately of the previous filter element 36, since this is automatically added to the pouch contents.

If preferred, the previous filter element 36 can be ejected before the new filter element 44 is inserted. For example, the tip of a pencil can be inserted into the bore to force the existing filter element 36 into the pouch.

In the above embodiment, the length of the filter element 36 has to be accommodated within the profile of the filter housing, the bore 28 being generally perpendicular to the plane of the flange 18. As explained above, the projecting "height" on the exterior of the pouch can be reduced by employing a rear extension of the housing, and "sinking" the bore 28 relative to the flange. Additionally, or alternatively, the bore 28 may be inclined diagonally relative to the flange, to accommodate the length of the bore 28 in a smaller "height" or housing thickness. Such modifications are illustrated in the fourth embodiment below.

Figure 6:
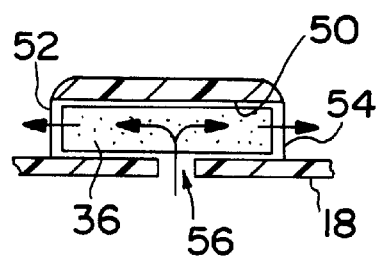
FIG. 6 is a schematic section view along the line VI—VI of FIG. 4.

In a second embodiment, referring to FIGS. 5 and 6, the filter receiving bore does not extend through the flange and into the pouch. Instead, the bore 50 extends generally parallel to the plane of the flange, adjacent to its outer surface. The opposite ends 52 and 54 of the bore 50 are both open to the exterior atmosphere, and gas enters the filter from the pouch through a central aperture 56 in the wall of the bore 50 and the flange 18. The gas flow divides into two opposite axial paths to the opposite ends 52 and 54 of the bore.

In this embodiment, the filter element 36 is similar to that described above (but it is a requirement that gas can enter the filter midway along its length). The filter element 36 is replaceable by inserting a replacement filter element (not shown) into one end of the bore, to force the previous filter element to be ejected through the opposite end. However, with this embodiment, the previous filter element 36 does not drop into the pouch, and will need to be disposed of separately. Nevertheless, such an arrangement does permit a gas-permeable, substantially liquid-impermeable barrier to be used (e.g. as illustrated in phantom by numeral 58) to prevent, or at least reduce, liquid contact with the filter.

Figure 7:
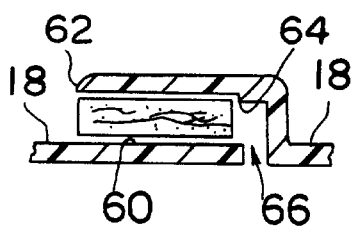
FIG. 7 is a schematic sectional view through a third embodiment of filter.

FIG. 7 illustrates a further embodiment which is similar to the second embodiment described above, but the bore 60 has only one end 62 open to the exterior atmosphere. The inner end 64 is closed, except for a passage 66 leading through the flange 18 and the pouch wall. In use, gas from the pouch vents through the passage 66, to the inner end 64 of the bore 60, and axially through the filter element 36 to the outer end 62 of the bore.

Although it is possible to extract the filter element 36 from the bore 60, and to insert a replacement filter element, this arrangement is more suited to filters which are intended not to be replaceable in use.

Figure 8:
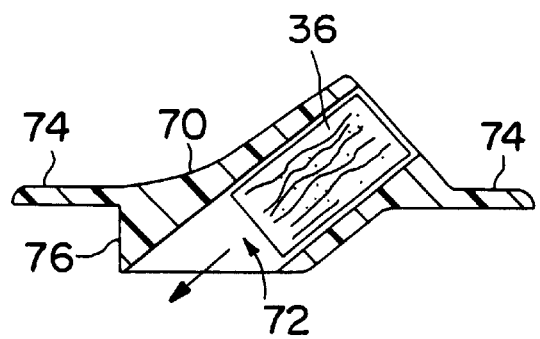
FIG. 8 is a schematic sectional view through a fourth embodiment of filter.

Although the above embodiments illustrate filter arrangements which are incorporated into a coupling member of the pouch, it will be appreciated that the same arrangements could be employed in discrete filters fitted to either the front or rear wall of a pouch. For example, FIG. 8 illustrates such a discrete filter embodiment. This is similar to the first embodiment described above, the filter housing 70 having a through bore 72 similar to the bore 28 to allow filter elements to be discharged into the pouch. In this embodiment, the housing includes a peripheral flange 74 to allow the housing 70 to be welded or adhered to a pouch wall. The housing also includes a rear extension 76 of the type discussed previously to reduce the projecting profile of the housing. The bore 72 is inclined diagonally relative to the flange 74, to further reduce the projecting profile of the housing.

Figure 9:
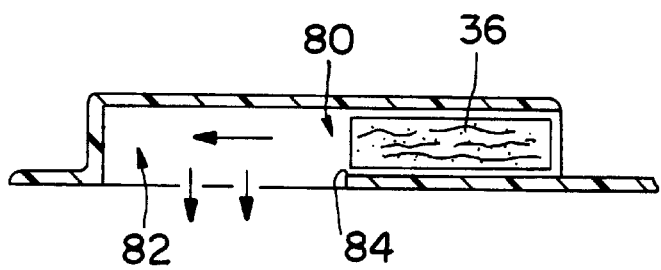
FIG. 9 is a schematic sectional view through a fifth embodiment of filter.

FIG. 9 illustrates a fifth embodiment which is similar to the fourth embodiment described above. However, in the fifth embodiment the bore 80 is generally parallel to the flange. A large open region 82 is provided at the inner end 84 of the bore 80 to allow a filter element discharged from the bore to fall sideways into the pouch. The length of the open region 82 is slightly greater than the length of the filter element, so that the filter element should be free to fall into the pouch. The open region 82 may be wider than the bore 80 so that there should be no tendency for the discharged filter element to stick to the wall of the housing.

It will be appreciated that the above designs of filter for a coupling member may also be used for a discrete filter, and the designs for a discrete filter may also be incorporated into a coupling member.

With the above embodiments, it is preferred that a range of filter elements having different flow rate characteristics be provided, to enable the ostomate to choose the best filter to suit his or her personal needs. It will be appreciated that different people produce different amounts of flatus, and this also depends on the type of food eaten. The filter should be able to vent flatus at such a rate to avoid the pouch ballooning under normal circumstances, but should also provide sufficient resistance to prevent collapsing of the pouch (which might cause the front and rear walls to stick together).

For example, each pouch could be accompanied by a packet of different filter elements to enable the ostomate to select the most appropriate filter. Alternatively, the ostomate may be able to purchase packets of filters separately. Particularly with the first, second and fourth embodiments described above, the filters may initially be supplied with a "standard" filter element, the ostomate having the opportunity to customise the filter by inserting a different filter element to suit his or her needs.

The filter could also be supplied initially with a solid plug element blocking the bore 28. The ostomate need then only fit a filter element if desired.

It will also be appreciated that the first, second and fourth embodiments described above provide a very simple way of replacing the filter element. The disposal into the pouch of the used filter element, provided by the first and fourth embodiments, is very hygienic and avoids the need to handle and dispose separately of the old filter element.

It will also be appreciated that this aspect of the invention, particularly as described in the preferred embodiments, can enable the use of novel type of filter which can be produced very economically by existing proven production facilities used normally in the cigarette filter industry.

Figure 10:
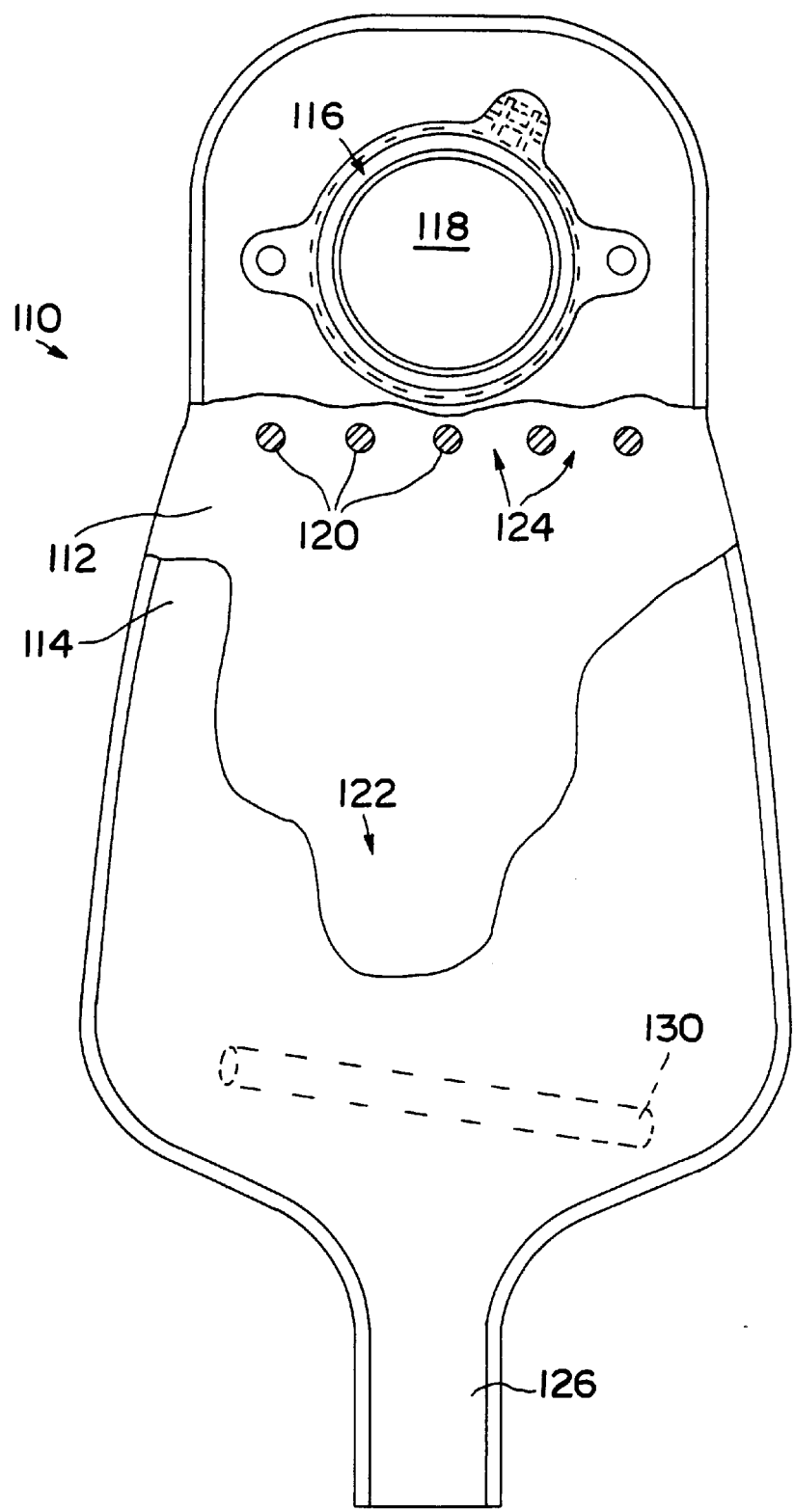
FIG. 10 is a partially cut away rear view of a urostomy pouch.

Referring to FIG. 10, a urostomy pouch 110 is formed by a front wall 112 and a rear wall 114 of plastics sheet, welded together around their periphery. A bagside connector 116 is secured to the rear wall 114 around a urine inlet aperture 118 in the rear wall 114. The connector 116 allows the pouch to be mechanically coupled to an adhesive bodyside component (not shown) worn by the ostomate.

Below the aperture 118 are a number of internal spot welds 120 securing the front and rear walls 112 and 114 together. The spot welds form a non-return, or anti-splash, valve for preventing urine in the main collection region 122 from splashing up to the aperture 118 a the wearer moves about. In the region of the spot welds 120, the front and rear walls are held in close contact with each other. Liquid entering the pouch through the aperture 118 is able to dribble through the gaps 124 between the spot welds, under gravity; however, liquid splashing inside the pouch is not able generally to pass back through the small gaps 124 (although the liquid might escape if the bag was inverted for any length of time).

Other forms of non-return valve may also be used, in particular other weld arrangements (for example as described in the above mentioned GB-A-2 268 882).

At the lower end of the pouch, the front and rear walls 112 and 114 define an integral outlet chute or tube 126 to facilitate emptying of the pouch. In normal use, the outlet tube 126 is closed by means of a conventional clip (not shown), which squeezes the walls together to form a liquid tight seal. In this embodiment, the tube 126 may be is relatively narrow, since the pouch will not be used to contain any solid matter.

Figures 11, 12:
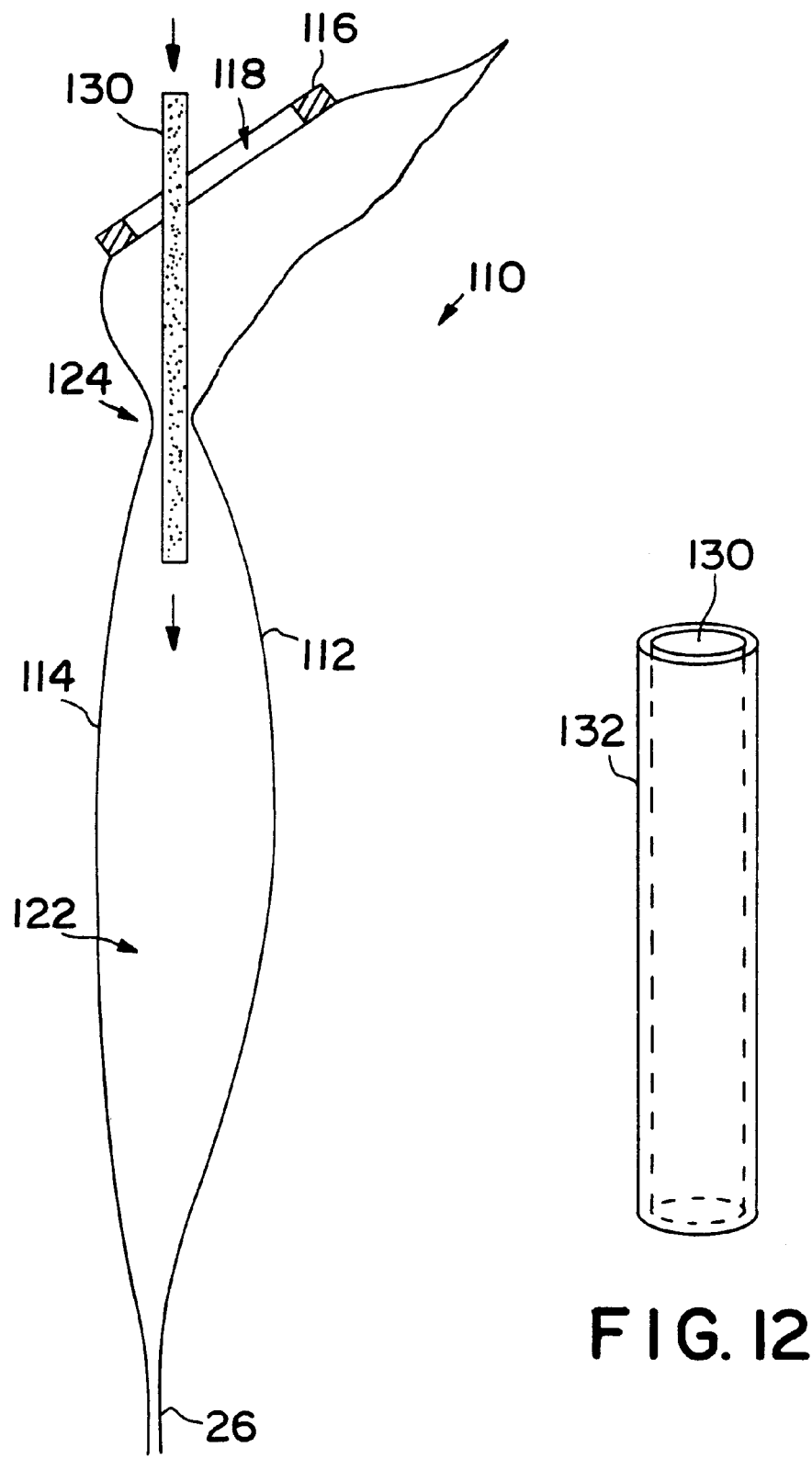
FIG. 11 is a schematic section illustrating introduction of a superabsorbent member into the pouch.
FIG. 12 is a schematic illustration of the superabsorbent member.

Referring to FIGS. 11 and 12, a superabsorbent member 130 is provided for insertion into the pouch. The member 130 is generally rigid, or semi-rigid, and is in the form of an elongate rod or stick. In this embodiment, the member 130 is generally cylindrical, having a diameter of between about 0.5 and about 2 cm, and a length of between about 2 and about 20 cm. The member 130 is sufficiently rigid to enable it to be introduced through the aperture, and forced through the non-return valve (i.e. through a gap 124 between two spot welds 120), into the liquid collection region 122 without the need for an applicator. This can be performed easily by hand, by inserting the member 130 endwise through the aperture, and advancing it downwardly. Once the member 130 has passed the non-return valve it sits in the liquid collection region 122 where it will gellify urine as the urine is collected in the pouch.

The superabsorbent member is preferably produced by the conventional production facilities used in the cigarette filter industry. By using a superabsorbent-containing, or superabsorbent-carrying, material packed into a wad, suitable elongate members can be formed by processing the material in the same way as in conventional cigarette filter production.

In the present embodiment, the material is water soluble, for example, polyvinyl alcohol. The member also includes a generally cylindrical outer sleeve, also of water soluble material, for example, polyvinyl alcohol. The sleeve serves to protect and contain the superabsorbent-containing material, and can assist retention of the member's shape.

In use, when urine contacts the member 130, the outer sleeve 132 dissolves, thereby allowing the superabsorbent material to contact, and gellify, the urine. The material on which the superabsorbent material is carried also dissolves, such that there are no solid parts remaining in the pouch contents, in this preferred embodiment. In other embodiments which may employ at least some non-soluble/non-gelling material in the member 130, debris may remain in the pouch and require disposal with the pouch contents when the pouch is emptied.

On emptying, the user would have to squeeze the pouch to ensure that all of the gelled material is discharged through the drain tube 126.

It will be appreciated that, if desired, a new member 130 could be introduced through the drain tube 126, for example, after emptying, rather than through the inlet aperture. In such case, the use of a rigid (or semi-rigid) elongate member 130 can simplify introduction, being more easily controllable, and reduce the risk of the user's hand's touching the wet inner surfaces of the pouch and being fouled by urine on the pouch walls.

Figure 13:
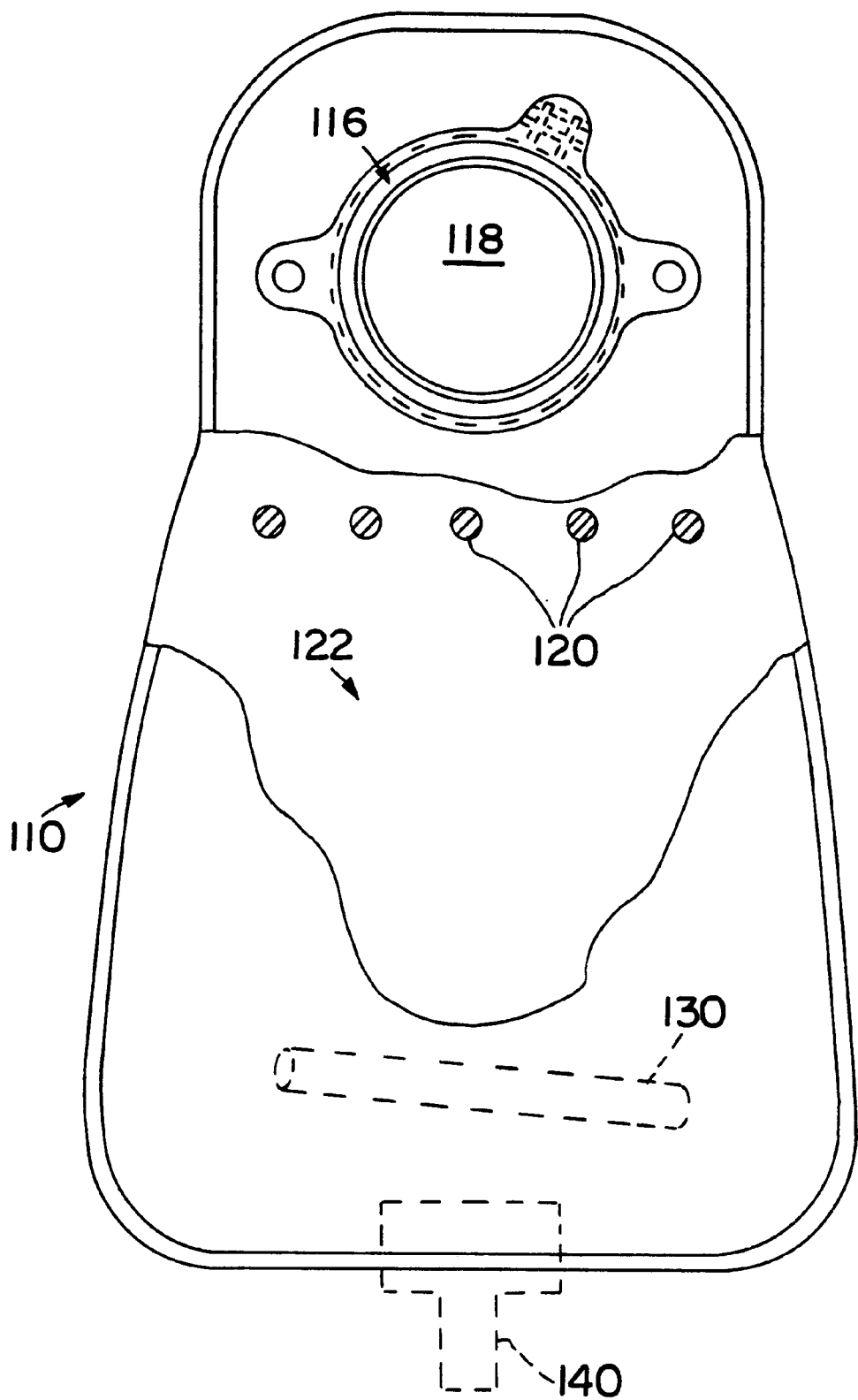
FIG. 13 is a partially cut away rear view of a second embodiment of a urostomy pouch.

FIG. 13 illustrates a second embodiment of urostomy pouch. This embodiment is very similar to the first embodiment described above, but the drain tube 126 is replaced by a tap positioned, for example on the front wall (shown schematically at 140). Many designs of tap are known in the art, varying from a narrow bore tube, which can be folded over to seal the tube (for example as illustrated in GB-A-2 058 011—Kingsdown Medical Consultants), to a multi-piece tap (for example, a rotatable tap as illustrated in GB-A-2 101 274—Craig Medical Products).

It will be appreciated that, with this embodiment, the superabsorbent member 130 can only be introduced through the inlet aperture, which emphasises the conventional problem of being able to manoeuvre the member through the non-return valve. The tap would be designed to enable the gelled contents of the bag to be forced through the tap upon squeezing the bag.

Figure 14:
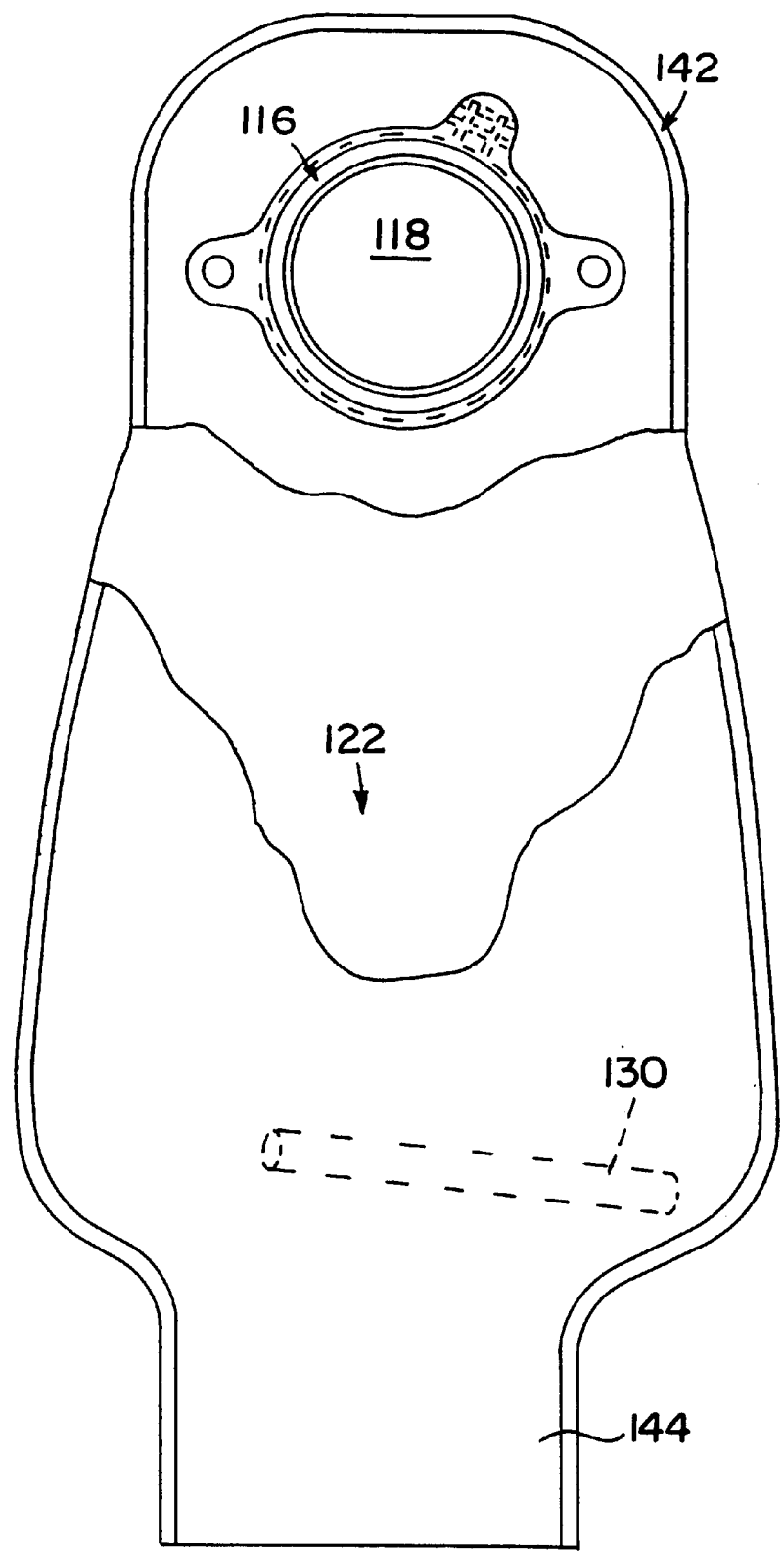
FIG. 14 is a partially cut away rear view of an ileostomy pouch.

FIG. 14 illustrates an ileostomy pouch 142. In contrast to a urostomy pouch, an ileostomy pouch is not normally provided with a non-return valve, and accordingly such a valve is omitted in this embodiment. The ileostomy pouch is similar to the first embodiment in that it has a drainage chute 144 at its lower ends, defined by the front and rear walls of the pouch. The drainage chute is closed in normal use by means of a clip (not shown). As can be seen in FIG. 14 the chute is generally wider than the chute 126 of the urostomy pouch, since the ileostomy pouch is required to be able to contain, at least some solid faecal matter, and to allow such solid matter to be emptied.

The ability to be able to manoeuvre an elongate rigid, or semi-rigid, superabsorbent member into the pouch (either through the inlet aperture, or through the drain chute 144) is especially advantageous for an ileostomy pouch, since after the initial use, the walls of the pouch will be contaminated with faecal slurry. It can be very unhygenic, unpleasant, and embarrassing for the wearer if his or her hands come into contact with the interior faces of the pouch walls when introducing the superabsorbent material. This is a serious problem when sheets of superabsorbent material are used, but can be overcome by using an elongate rigid, or semi-rigid, stick or rod member as in the present invention.

It will be appreciated that this aspect of the present invention can provide a superabsorbent member, or a superabsorbent-containing member, which is simple and clean to introduce manually into a pouch, even a urostomy pouch or an ileostomy pouch, without requiring the use of an applicator. Of course, if desired, an applicator can be used for reasons of hygiene. The superabsorbent member can be produced compactly, using conventional production facilities used in the cigarette filter industry, which means that production costs need not be expensive.

Although features and aspects of the invention believed to be of particular importance have been set out in the forgoing description and in the appended claims, the Applicant claims protection for any novel idea, feature or combination of features described herein or illustrated in the accompanying drawings irrespective of whether emphasis has been placed thereon.

I claim:

1. An ostomy pouch coupling member for attaching an ostomy pouch to a complementary coupling member worn on the body, the ostomy pouch coupling member including a deodorizing filter assembly; the assembly comprising a filter housing having a bore therein, said bore having two opposite open ends, one open end opening external to the ostomy pouch, the other open end opening internal to the ostomy pouch, an elongated filter element receivable longitudinally within the bore, said filter element being insertable into the bore by sliding the filter element through said external open end into said bore, said filter element being ejectable through said internal open end into the ostomy pouch.

2. The coupling member according to claim 1, wherein the bore has a longitudinal dimension greater than a lateral dimension.

3. The coupling member according to claim 1, wherein a gas flow path through the filter element is generally in an axial direction.

4. The coupling member according to claim 1, wherein the bore and the filter element are generally cylindrical.

* * * * *